United States Patent [19]

Sifniades

[11] 3,931,308

[45] Jan. 6, 1976

[54] PROCESS FOR CONVERSION OF LYSINE DIHYDROCHLORIDE TO LYSINE MONOHYDROCHLORIDE

[75] Inventor: Stylianos Sifniades, Parsippany, N.J.

[73] Assignee: Allied Chemical Corporation, New York, N.Y.

[22] Filed: May 28, 1974

[21] Appl. No.: 473,453

Related U.S. Application Data

[63] Continuation-in-part of Ser. No. 368,007, June 7, 1973, abandoned.

[52] U.S. Cl. ............... 260/534 L; 260/239.3 A
[51] Int. Cl.²C07C 99/00; C07C 99/06; C07C 99/12
[58] Field of Search .......................... 260/534 L

[56] References Cited
UNITED STATES PATENTS

| | | | |
|---|---|---|---|
| 2,556,917 | 6/1951 | Hambrock | 260/534 L |
| 2,564,649 | 8/1951 | Rogers | 260/534 L |
| 2,876,218 | 3/1959 | Francis et al. | 260/534 L |
| 3,576,859 | 4/1971 | Nelemans | 260/534 L |

*Primary Examiner*—Vivian Garner
*Attorney, Agent, or Firm*—Roger H. Criss; Arthur J. Plantamura

[57] ABSTRACT

Lysine dihydrochloride solution, formed by the hydrolysis of α-amino-ε-caprolactam, is converted to crystalline lysine monohydrochloride by neutralization with α-amino-ε-caprolactam or a transition metal complex thereof and crystallization from the solution with an organic solvent. After removal of the precipitated lysine monohydrochloride, the remaining solution is fractionated and that fraction consisting essentially of the by-product of the neutralization may be recycled to ensure recovery of substantially all the desired product and utilization of all processing agents.

12 Claims, 3 Drawing Figures

PROCESS FOR CONVERSION OF LYSINE DIHYDROCHLORIDE TO LYSINE MONOHYDROCHLORIDE

CROSS-REFERENCE TO RELATED APPLICATION

This application is a continuation-in-part of my copending application Ser. No. 368,007, filed June 7, 1973, now abandoned.

BACKGROUND OF THE INVENTION

The present invention relates to a method for converting L-lysine·2HCl to L-lysine·HCl.

L-lysine is one of the nutritionally essential amino acids. Its widespread use as a dietary supplement has unfortunately been inhibited by the difficulty of synthetically producing it economically and efficiently.

It is known to produce lysine by hydrolysis of certain precursors with hydrochloric acid. It has been found that in order to obtain a good rate of hydrolysis, it is necessary to use at least 2 mols HCl per mol precursor. As a result, the lysine produced is present in the reaction mixture as a dihydrochloride salt, rather than as the desired monohydrochloride salt.

A variety of methods have been suggested for removal of the extra HCl. In accordance with one method, as disclosed in U.S. Pat. No. 2,876,218, lysine dihydrochloride is first isolated by hydrolyzing α-amino-ε-caprolactam and subjecting the hydrolysis mixture, which contains lysine dihydrochloride and hydrochloric acid, to a vacuum distillation, and subsequently the lysine dihydrochloride is converted to lysine monohydrochloride by use of pyridine in an alcoholic medium. A similar method of conversion is disclosed in U.S. Pat. No. 2,564,649. In the latter case the lysine precursor is 5 (α-aminobutyl) hydrantoin hydrochloride. The recovery of the alcohol and pyridine used, as well as of the hydrochloric acid split from the lysine dihydrochloride requires a number of costly operations. This process suffers from the decided disadvantage that the separation steps, noted above, are expensive and time-consuming and the process, therefore, is hardly usable for the industrial-scale preparation of lysine monohydrochloride from α-amino-ε-caprolactam. Additionally, the pyridine weak base hydrochloride is formed as a byproduct and must also be removed.

U.S. Pat. No. 2,579,283 teaches the production of lysine by hydrolysis of a polymeric hydantoin followed by the conversion of lysine dihydrochloride to lysine monohydrochloride by passing an aqueous solution of the dihydrochloride over an anion exchange resin. The resin is then regenerated to yield a chloride solution; however, there is no way to recover the processing agents, e.g. ammonium hydroxide, sodium hydroxide or other bases, which were employed to regenerate the resin. When it became known to use L-aminocaprolactam as a satisfactory lysine precursor, the use of an ion exchange resin was expanded in U.S. Pat. No. 3,576,859 to include the recovery and reutilization of the processing agents. In this patent, the lysine dihydrochloride, produced from the hydrolysis of α-amino-ε-caprolactam, is passed through an anion exchanger to remove HCl. Then, the HCl bound to the resin is removed by formation of a salt with additional α-amino-ε-caprolactam and the salt is then reused in the hydrolysis step. However, both of these patents have the disadvantage of necessitating bulky, costly and time-consuming anion exchange resin equipment. Moreover, the lysine monohydrochloride thus formed is obtained as a relatively dilute aqueous solution which must be further processed to recover the lysine monohydrochloride in the desired form.

Additionally, all these methods require that the lysine precursor be completely hydrolyzed to lysine·2HCl to prevent the occurrence of any yield loss and/or product contamination during the subsequent conversion steps and/or recycling operations. Since the hydrolysis proceeds at an exponentially decreasing rate, the necessity for hydrolysis of the last 5–10 percent of the lysine precursor renders the operation more difficult and time-consuming.

Not withstanding the various prior methods, the method of the present invention affords a definitely advantageous alternative by producing an economical, efficient and relatively fast method of converting lysine dihydrochloride to lysine monohydrochloride.

The method of the present invention is also advantageous in that it produces lysine monohydrochloride in a system which does not require complete hydrolysis of the lysine precursor.

Moreover, the present invention provides a method for the conversion of lysine dihydrochloride to lysine monohydrochloride in which a lysine precursor is used as the neutralizing agent thereby ensuring the complete utilization of all the processing materials.

SUMMARY OF THE INVENTION

I have found that lysine dihydrochloride (L-Ly·2HCl), particularly an aqueous solution of lysine dihydrochloride which has been produced by the hydrolysis of α-amino-ε-caprolactam (ACL) with more than 2 mols hydrochloric acid per mol α-amino-ε-caprolactam precursor, can be converted to crystalline lysine monohydrochloride (L-Ly·HCl) by neutralization of the solution with α-amino-ε-caprolactam or a transition metal complex thereof and crystallization of lysine monohydrochloride from the solution by addition of an organic solvent. After removal of the precipitated crystalline lysine monohydrochloride the remaining solution containing the neutralization by-products may be utilized in one of the following ways:

a. If the neutralization is carried out using L-ACL, the solution is fractionated, the organic solvent recycled to the neutralization and the fractionation residue containing primarily L-ACL·HCl is recycled to the hydrolysis step without further isolation.

b. If the neutralization is carried out using other than the optically pure L enantiomer, e.g. a racemic modification of D, L-ACL or D-ACL, the solution is fractionated to separate the organic solvent which is recycled to the neutralization and a portion of the water, the fractionation residue is filtered to remove the precipitated crystalline D,L-ACL·HCl or D-ACL·HCl which is recycled to a resolution operation and the filtrate is recycled to the neutralization step.

c. If the neutralization is carried out using L-ACL-transition metal complex or an optically impure L-ACL-transition metal complex, the solution remaining after removal of the precipitated lysine monohydrochloride is dried, and the organic solvent recycled. The remaining crystalline residue is then extracted with an alcohol to separate the crystalline L-ACL·HCl from the alcohol solution containing the transition metal salt; the extraction residue containing primarily crystalline L-ACL·HCl is recycled to the hydrolysis step and the alcohol extract containing primarily the transition metal salt and any D,L-ACL·HCl, if present, is recycled to a resolution operation.

The neutralization-crystallization process of the present invention is preferably carried out by adding the aqueous lysine dihydrochloride solution to a solution of α-amino-ε-caprolactam in an organic solvent. Lysine monohydrochloride crystallizes out and is removed. The α-amino-ε-caprolactam hydrochloride solution is first fractionated to recover the organic solvent and then either recycled to the hydrolysis step or α-amino-ε-caprolactam hydrochloride is crystallized out and recycled to a resolution process.

In accordance with the invention, the lysine dihydrochloride solution is preferably subjected to a distillation step prior to neutralization with α-amino-ε-caprolactam or transition metal complex thereof. The purpose of the distillation is to remove the excess free HCl which was utilized in the hydrolysis step. This distillation step also results in the conversion of a small amount of the dihydrochloride to the monohydrochloride. If the distillation step is not employed, the excess free HCl may be removed at other stages during the conversion process using other conventional techniques such as ion-exchange resins, etc. However, for the purpose of simplicity, economics and ease of operation, the distillation prior to neutralization-crystallization is most satisfactory.

The primary advantage of the present conversion technique is that it allows full utilization of all the processing agents employed. Thus, relatively pure lysine monohydrochloride is precipitated in crystalline form out of the system and the remaining aqueous-organic solution is easily fractionated to separate out the organic solvent which is recycled to the crystallization step. Then, the remaining aqueous solution containing primarily α-amino-ε-caprolactam monohydrochloride is either recycled to the hydrolysis or neutralization step or recovered for use as feed in a subsequent resolution operation.

Another advantage of the present invention is that since the α-amino-ε-caprolactam is utilized in both the hydrolysis and the neutralization steps, it is possible to carry out the hydrolysis step to only partial conversion, e.g. until at least about 80% of the precursor is converted to lysine-dihydrochloride and allow the remaining unconverted α-amino-ε-caprolactam to be recycled.

Thus, in accordance with the method of the present invention, I have found a way of utilizing the lysine precursor to act downstream as the neutralizing agent without the use of resins or other complicated means to separate the processing agents from the lysine-producing system.

DESCRIPTION OF THE DRAWINGS

The three figures represent flowsheets showing various preferred embodiments of the continuous operation of the present invention.

DESCRIPTION OF THE PREFERRED EMBODIMENTS

Figure 1:
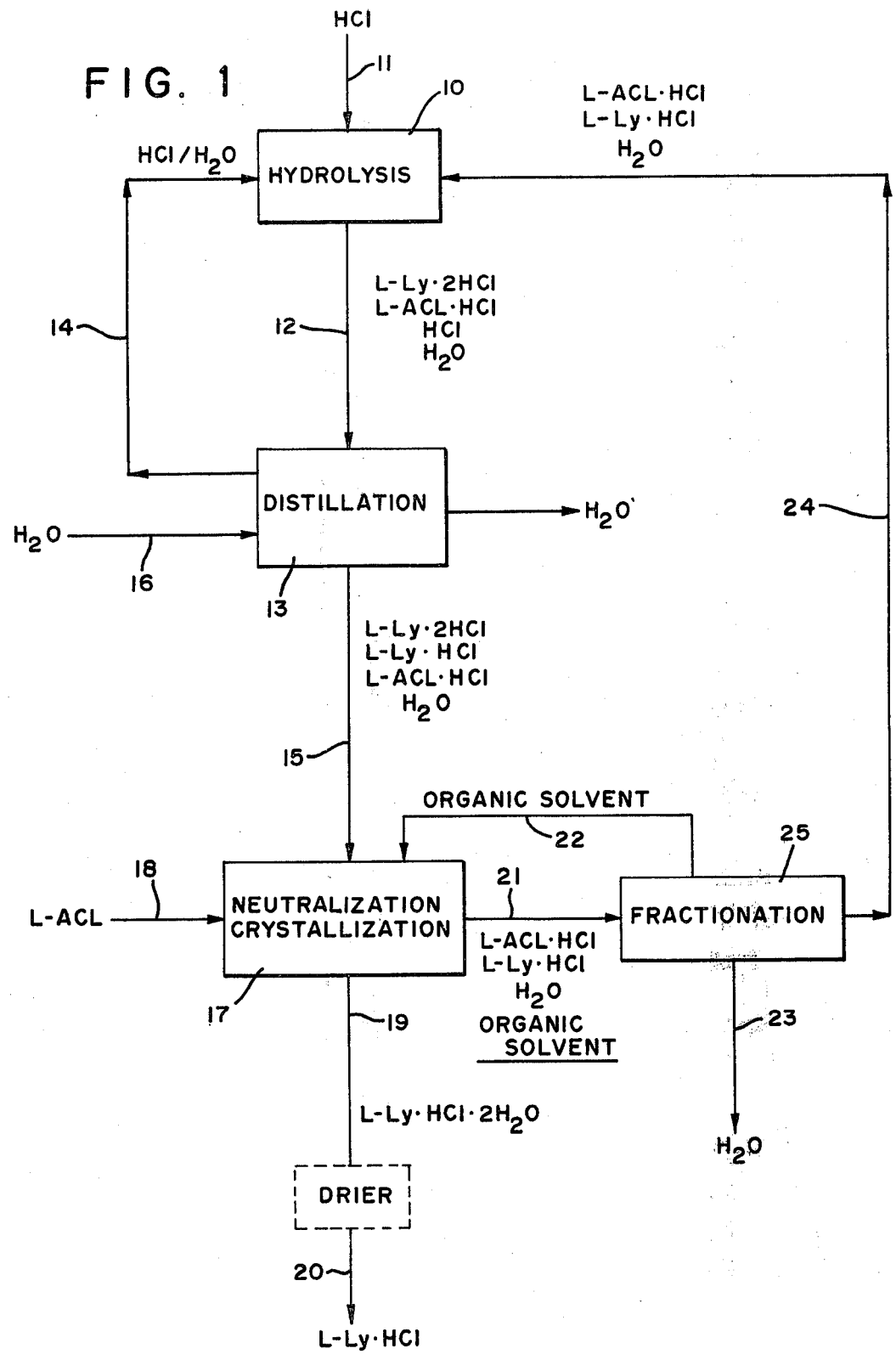

A basic hydrolysis operation is employed with all the various embodiments of the present invention. Referring to any of FIGS. 1, 2, and 3, the L-α-amino-ε-caprolactam is hydrolyzed (10) in an aqueous solution with more than 2 mols HCl (11) per mol of lactam at any convenient temperature. I have found that the reaction proceeds well under pressure of about 5 to 100 psig. If desired, the hydrolysis may also be carried out at atmospheric pressures under reflux conditions. In either case, the temperature should be from the boiling point of the solution to around 160°, preferably about 140°. The reaction is allowed to proceed until at least about 80 percent of the lactam has been hydrolyzed (12) as determined by thin layer chromatography and/or measurement of the specific optical rotation.

The hydrochloric acid in the hydrolysis mixture which is not bound to the lysine can be removed in a variety of ways. U.S. Pat. No. 3,576,859 teaches the removal by distillation (13) at 95°–120°C. The reference further teaches that sufficient hydrochloric acid (14) can be removed so that the hydrolysis mixture (15) which is to be converted to L-lysine·HCl will contain at least some lysine monohydrochloride, preferably about 0.05–0.3 mol (monohydrochloride per mol dihydrochloride) in addition to the lysine dihydrochloride. This is effected by continuously replacing with water (16) at least part of the aqueous HCl which is removed during distillation.

The novel neutralization procedure used in the present invention may employ α-amino-ε-caprolactam as either of its enantiomers or in its impure racemic form which will comprise a mixture of both the D and L enantiomers and which for convenience will henceforth be referred to as D,L-ACL with the understanding that this does not necessarily imply a 50—50 mixture of the D and L enantiomers, with the subsequent recovery steps dependent upon just which form is used, as will be described below with respect to each optical form.

It is obvious that in accordance with any of the following descriptions, a one- or two-step neutralization crystallization operation can be employed; however, the one-step process which involves the addition of the neutralizing agent in a solution of the organic solvent is preferred since it is more economical to operate. Thus, each of the flowcharts will be described using the one-step neutralization crystallization.

The flowchart in FIG. 1 shows the use of L-ACL as the neutralizing agent. According to this procedure, the neutralization-crystallization (17) step is carried out using a solution of L-α-amino-ε-caprolactam (18) in an organic solvent (22). The solvent should be miscible with water to at least about 30 percent by volume. The solvent should preferably have a boiling point lower than water or be capable of forming an azeotrope with water. The preferred solvent would be alcoholic in nature but certain ether media such as glyme could also be employed. For reasons of economy and availability, the $C_1$ to $C_3$ alcohols, such as methanol, ethanol, n-propanol and isopropanol, or mixtures thereof, are preferred. However, other organic solvents may be employed, such as linear and cyclic ethers and polyethers, such as alkyl and cycloalkyl mono- and diethers of 2 to 12 carbon atoms, such as 1,2-dimethoxyethane (i.e., glyme), 1,4-dioxane, tetrahydrofuran, and the like, as well as amides of $C_1$ to $C_3$ carboxylic acids, such as dimethylformamide, as well as mixtures of these solvents. Sufficient solution should be utilized to provide at least a molar equivalent of lactam per mol lysine dihydrochloride. The reaction is carried out under any convenient temperature and pressure conditions. The preferred temperature range is from about 20°–75°C. Lower temperatures could be utilized but no advantage would ensue. At temperatures of about 60°C., more concentrated volumes may be used to give higher rates of crystallization.

After crystallization, the L-lysine·HCl·2H$_2$O (19) is purified by washing with fresh aqueous-organic solvent, dried and recovered as L-lysine HCl (20). The remaining solution containing L-α-amino-ε-caprolactam HCl and some L-lysine·HCl (21) is subjected to fractionation (25), as by distillation, and the organic solvent (22) recycled back to the crystallization step (17). A small amount of water (23) is recovered and may be recycled to effect partial removal of HCl in the first distillation (13) and the remaining aqueous mixture of L-α-amino-ε-caprolactam HCl (24) and L-lysine·HCl recycled to hydrolysis (10) where addition of HCl will result in conversion to L-lysine dihydrochloride (12).

Figure 2:
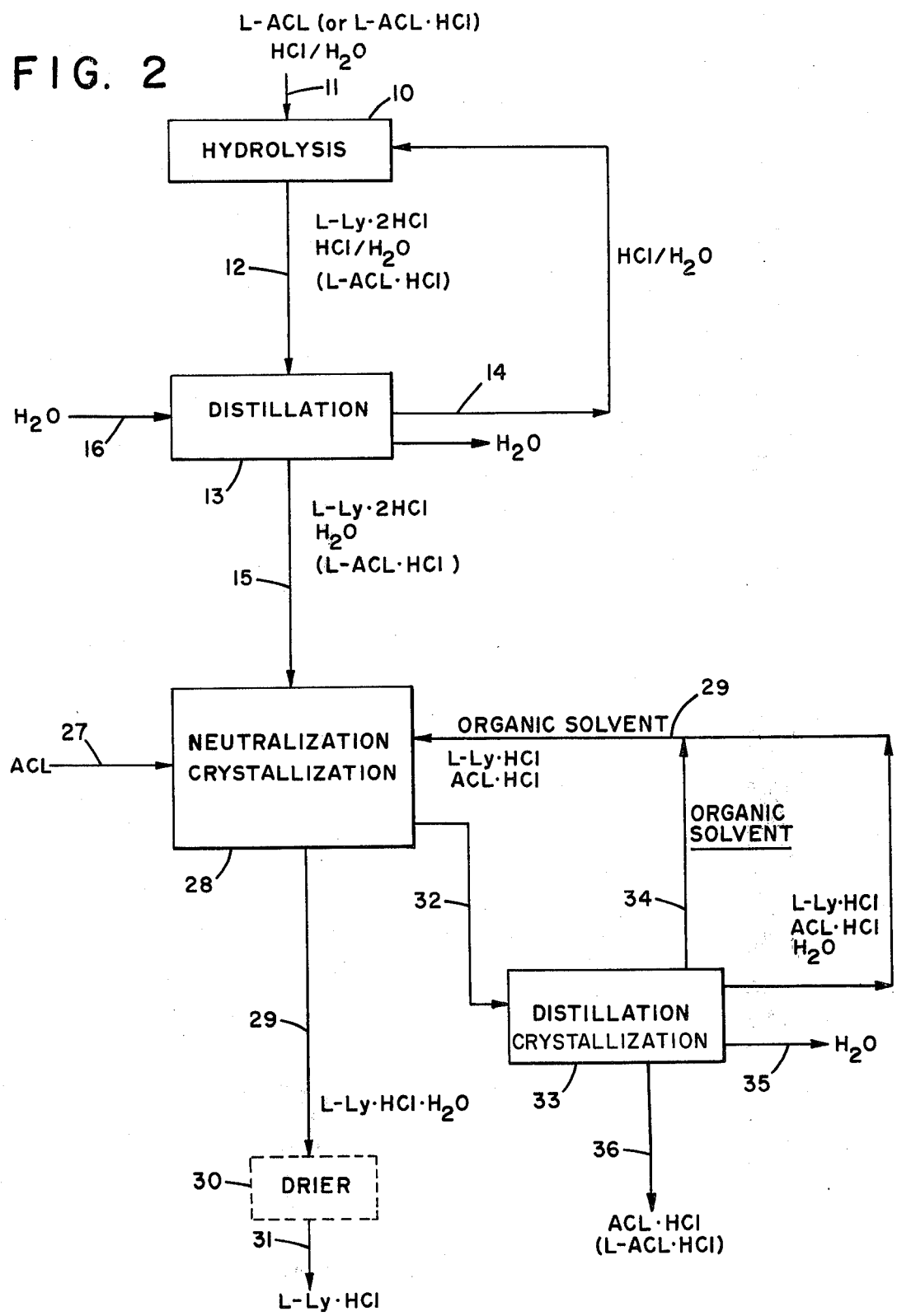

In accordance with the procedure of FIG. 2, lysine dihydrochloride is neutralized to the monohydrochloric using A-ACL or the D, L-racemic modification of the ACL as previously described. The ACL used herein could, of course, be in the L form but in that case it would be more economical to use the procedure described in accordance with FIG. 1. The D-ACL or D,L-ACL may be employed in this embodiment since the ACL introduced as neutralizing agent is not recycled immediately to the hydrolysis but instead, is recovered as D-ACL·HCl or D,L-ACL·HCl. This procedure is particularly advantageous in combination with a resolution process utilizing D,L-ACL·HCl as the resolving species. This combination saves one mol of HCl which would be used to prepare D,L-ACL·HCl from D,L-ACL.

Referring to FIG. 2, ACL (27) is added to the neutralization reactor (28) together with a recycle solution (29) containing the organic solvent and aqueous solution of L-lysine·HCl and ACL·HCl. The bulk of the neutralized L-lysine·HCl crystallizes out as L-lysine HCl·2H$_2$O (29) which may optionally be dried (30) and recovered as L-lysine·HCl (31). The mother liquor (32) is subjected to distillation (33) where the organic solvent (34) is distilled off and recycled to the neutralization/crystallization reactor (28). The same organic solvents referred to above may be used. Some water is also distilled off at this time (35). Most of the ACL·HCl (36) separates out as crystalline product and is filtered while the mother liquor (29) is recycled to the neutralization reactor (28). This recycling ensures full recovery of both L-lysine HCl and ACL·HCl. For optimum economy in operation, the crystalline ACL·HCl produced herein is resolved using the methods known in resolution procedures.

Figure 3:
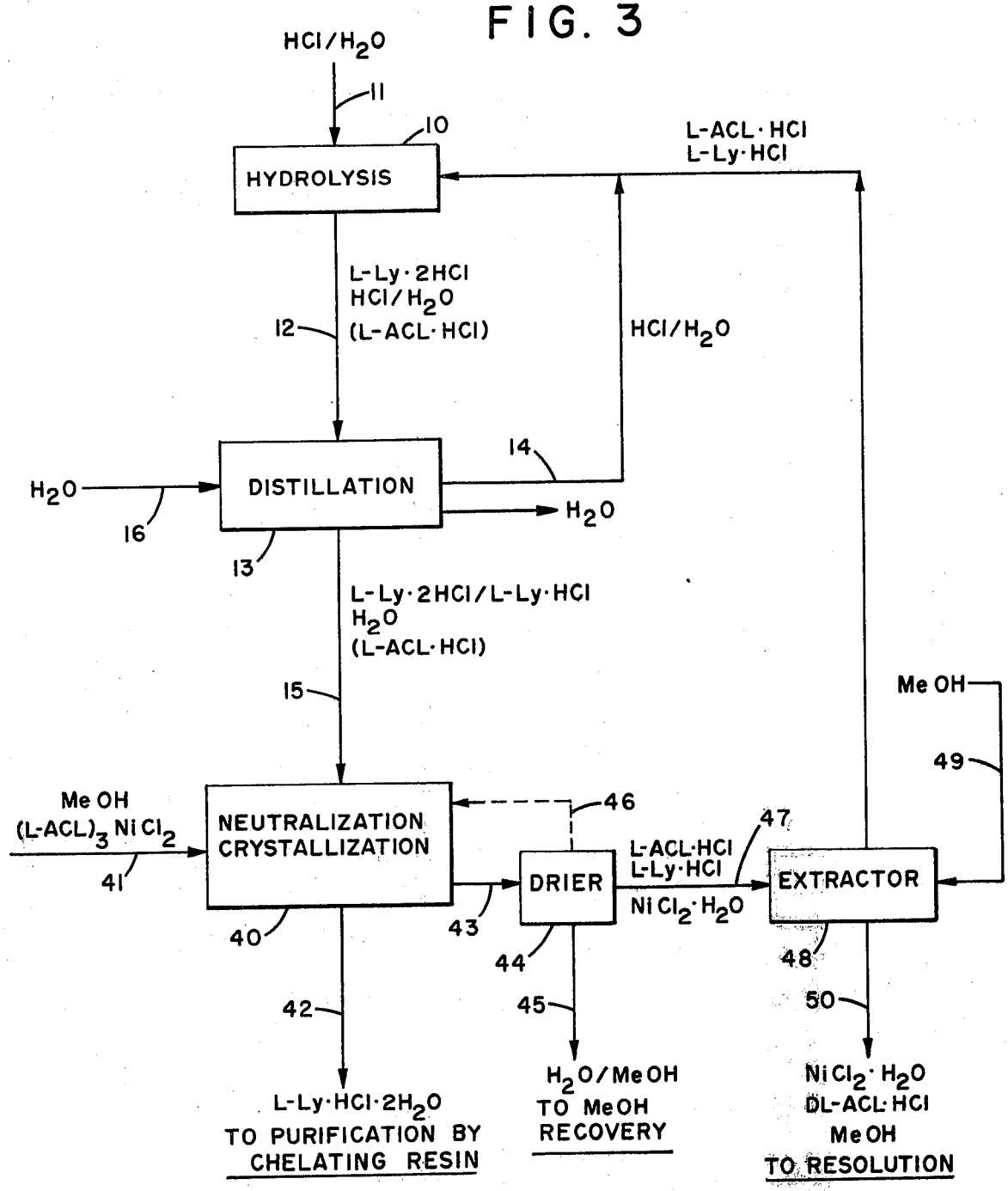

FIG. 3 represents an alternative embodiment of the present invention in which the L-ACL used as the neutralizing agent is present in the form of a transition metal complex chloride salt. Examples of such chlorides are complexes with transition metal ions, such as Ni$^{+2}$, Co$^{+2}$, Cu$^{+2}$, Fe$^{+2}$, Fe$^{+3}$, Fe$^{+3}$ and Zn$^{+2}$. Preferred are the NiCl$_2$ and CoCl$_2$ complexes. This embodiment is particularly advantageous when used with the resolution procedure described in U.S. application Ser. No. 301,409, filed Oct. 27, 1972, now U.S. Pat. 3,824,231 issued July 16, 1974, which is incorporated herein by reference, since the neutralization by-products, i.e., NiCl$_2$, H$_2$O, DL-ACL·HCl and alcohol are the starting materials required for the resolution procedure described therein. Moreover, the L-ACL metal salt may be optically impure and may contain up to about 10 % D-ACL when used as neutralizing agent since any D,L-ACL produced from the impurities is withdrawn from the system and the remaining L-ACL is upgraded by extraction with methanol. Thus, any L-ACL which is recycled to the hydrolysis operation is optically pure. It is, of course, understood that the ACL metal salt could also be used in the form of its D-enantiomer if this is the desired form for recovery.

Referring to FIG. 3, the distillation bottoms (15) containing L-Ly·2HCl, some L-Ly·HCl, H$_2$O and possibly some L-ACL·HCl are fed into the neutralization reactor (40) together with an alcoholic solution containing an alcohol of 1 to 3 carbon atoms. (here represented as MeOH) of optically impure (L-ACL)$_3$NiCl$_2$ (41). After filtration, the bulk of the L-lysine·HCl is separated as crystals of L-Ly·HCl·2H$_2$O (42) which contain trace amounts of NiCl$_2$ which can be easily removed by treatment, as for example, with a chelating resin. The filtrate (43) is dried (44) using 2 spray-drier, film evaporator, drum-drier, etc. and the water and methanol either recovered (45) or recycled (46) to the neutralization operation (40). The dry residue (47) consisting of optically impure L-ACL·HCl, some L-Ly·HCl and NiCl$_2$ hydrate is extracted (48) with methanol (49) or other lower alcohol. The extract (50) containing NiCl$_2$·H$_2$O, DL-ACL·HCl and traces of L-Ly·HCl is then recycled to the resolution operation. The solid residue (51) containing optically pure L-ACL·HCl, small amounts of L-Ly·HCl, and traces of NiCl$_2$ is then recycled to the hydrolysis operation (10).

The following examples are for the purposes of illustration and the scope of the invention is not meant to be limited thereto. For the purposes of the following examples, the term L-ACL is used to represent L-α-amino-ε-caprolactam.

EXAMPLE I

Hydrolysis

L-ACL·HCl, 197 g (1.2 mol) and 6N hydrochloric acid, 400 ml (2.4 mol) were placed in a 1 l. autoclave and heated at 142°C. for 80 minutes. At the end of the period all L-ACL·HCl had been converted to L-lysine·2HCl. No racemization took place.

Distillation 1

The reaction mixture was subjected to distillation at atmospheric pressure. During distillation, the amount of water that distilled off together with HCl was partly replaced by periodic additions of fresh water. 51.2 grams (1.4 mol) HCl distilled. This HCl was then recycled to the hydrolysis step.

Neutralization-crystallization

The residue contained 219 g (1 mol) L-lysine·2HCl, 36.5 g (0.2 mol) L-lysine·HCl and 360 ml. water. To this was added a solution of L-ACL, 128 g (1 mol) in 1000 ml. methanol. Crystals of L-lysine·HCl·2H$_2$O started forming immediately. The crystallization was completed after 30 minutes at room temperature, the crystals were filtered and washed with MeOH:H$_2$O (4:1) and dried at 120°C. The yield of L-lysine·HCl was 182.5 g (1 mol).

Distillation 2

The combined mother liquors and wash liquors were fractionated. Almost pure MeOh, 1000 ml., was obtained. The residue contained 164.5 g (1 mol) L-ACL·HCl and 36.5 g (0.2 mol) L-lysine·HCl in water. This solution, after adequate concentration, was treated as described in the above hydrolysis step, with HCl in an autoclave to produce more L-lysine·2HCl.

EXAMPLE II

L-ACL·HCl, 197 g (1.2 mol) was refluxed with 400 ml. 6N hydrochloric acid (2.4 mol). After 2 hours, 96 percent of the L-ACL·HCl had been converted to L-lysine·2HCl. Subsequent distillation of HCl as in Example I followed by neutralization with 123 g (0.96 mol) of L·ACL in 1000 ml. methanol and subsequent filtration and drying of the crystals at 120°C. yielded 177 g (0.97 mol) L-lysine·HCl. The mother liquor contained 167 g (1.01 mol) L-ACL·HCl and 32.9 g (0.18 mol) L-lysine·HCl. This solution, afer distillation of methanol and some water, could be refluxed with HCl as described above to produce more L-lysine·2HCl.

EXAMPLE III

A two-step crystallization procedure is described in the following example. Crystalline L-ACL, 128 g (1 mol) was added to a solution of 219 g (1 mol) of L-lysine·2HCl in 350 ml. water. The temperature rose to approximately 50°C. as L-ACL dissolved. On cooling to room temperature, crystals of L-ACL·HCl formed. The crystals were filtered after 15 minutes at 25°C. and washed with a little cold water and dried. Yield of L-ACL·HCl was 69 g (0.42 mol). At the same time about 3 g L-Ly·HCl crystallized out. The combined crop could be recrystallized from water to yield pure L-ACL·HCl. Alternately, it could be hydrolyzed with HCl to produce more L-lysine·2HCl. Ethanol, 1000 ml., was added to the combined liquor. On standing for 30 minutes at room temperature, filtering and drying, 165 g (0.90 mol) L-Lysine·HCl crystals were obtained and collected by filtration. The mother liquors contained 15.3 g (0.084 mol) L-lysine·HCl and 95 g (0.58 mol) L-ACL·HCl. After distilling off the ethanol and some water, these liquors could be hydrolyzed with HCl to produce more L-lysine·2HCl.

EXAMPLE IV

This example shows the use of a racemic mixture of D,L-ACL in the method of the present invention to produce L·Ly·HCl.

The procedure of Example I was repeated using 1 mol (128 g) D,L-ACL in the neutralization step. L-lysine·HCl, 1 mol (182.5g) was obtained upon filtration and drying. Distillation of the resulting filtrate yielded 164.5 g (1 mol) D,L-ACL·HCl and 36.5 g (0.2 mol) L·lysine HCl in about 100 ml. of water. After cooling, filtering and washing with cold water, 110 g. crystalline D,L-ACL·HCl were recovered. The mother liquor containing the balance of the L-lysine HCl and D,L-ACL·HCl, was recycled to the neutralization step.

EXAMPLE V

In order to show that the D-enantiomer of ACL can be used in the present invention, the procedure of Example IV was repeated using 1 mol of D-ACL as the neutralizing agent. 120 Grams of crystalline D-ACL·HCl were recovered as well as 182.5 g L-lysine HCl.

EXAMPLE VI

The use of the L-ACL transition metal complex as neutralizing agent is shown in this example. L-ACL·HCl, 165 g (1 mol) was heated in an autoclave at 141°C. with 2 mols of 4N hydrochloric acid (500 ml.). After 15 minutes, 91 percent of L-ACL·HCl had been converted to L-Lysine-2·HCl. The reaction mixture was subjected to distillation in order to eliminate excess HCl. The residue, containing 199 g (0.91 mol) L-Lysine HCl and 14.8 g (0.09 mol) L-ACL·HCl in about 330 ml. water, was mixed with 1000 ml. of a deep blue methanol solution of 156 g (0.303 mol) (L-ACL)$_3$NiCl$_2$ of optical purity 95 percent. The color changed to pale green and the temperature of the mixture rose spontaneously to about 40°C. After cooling to room temperature and standing for about 15 minutes, the mixture was filtered and the crystals of L-Lysine-HCl·2H$_2$O were washed with a little methanol and dried at 120°C. The resulting L-Lysine HCl weighed 126 g (0.69 mol). This represents 76 percent recovery of the L-Lysine produced in the hydrolysis. The combined liquor was subjected to spray-drying. The dry residue which contained 2 to 5 percent water was treated for 30 minutes with 560 ml. of refluxing methanol. After cooling to room temperature, the mixture was filtered and the crystals were washed with a little methanol and dried at 120°C. The dried crystals weighed 189.3 g and were composed of 151 g (0.92 mol) L-ACL·HCl of 100 percent optical purity and 38.3 g (0.21 mol) L-Lysine·HCl These crystals could be recycled to the hydrolysis reactor. The mother liquor contained 13.1 g (0.08 mol) L-ACL·HCl of low optical purity, 39 g (0.302 mol) NiCl$_2$ and small amounts of L-Lysine·HCl. This solution could be recycled to form fresh (D,L-ACL)$_3$NiCl$_2$ which would then be resolved to (L-ACL)$_3$NiCl$_2$ and recycled.

EXAMPLE VII

The procedure of Example VI is repeated using (L-ACL)$_3$CoCl$_2$ as the neutralizing agent. Similar high recovery of L-lysine·HCl, L-ACL·HCl and CoCl$_2$ are obtained.

It is to be understood that variations and modifications of the present invention may be made without departing from the scope of the invention. It is also to be understood that the scope of the invention is not to be interpreted as limited to the specific embodiment disclosed herein, but only in accordance with the appended claims when read in light of the foregoing disclosure.

I claim:

1. In a method for converting an aqueous solution of lysine dihydrochloride to crystalline lysine monohydrochloride wherein the lysine dihydrochloride is produced from the hydrolysis of α-amino-ε-caprolactam, or α-amino-ε-caprolactam hydrochloride with more than two mols of hydrochloric acid per mol of α-amino-ε-caprolactam, the improvement comprising the steps of:
   a. neutralizing said solution with α-amino-ε-caprolactam or a transition metal complex chloride salt thereof;
   b. crystallizing lysine monohydrochloride from said solution by addition of an organic solvent; and
   c. removing the precipitated crystalline lysine monohydrochloride.

2. The method of claim 1 wherein the lysine dihydrochloride solution is subjected to a distillation step prior to neutralization to remove excess HCl.

3. The method of claim 1 wherein the lysine dihydrochloride solution contains up to about 20 percent unhydrolyzed α-amino-ε-caprolactam or α-amino-ε-caprolactam hydrochloride.

4. The method of claim 1 wherein said organic solvent is chosen from the group consisting of an alcohol or ether.

5. The method of claim 4 wherein said organic solvent is chosen from the group consisting of methanol, ethanol, n-propanol, isopropanol, or mixtures thereof.

6. The method of claim 1 wherein the lysine dihydrochloride is neutralized in a solution consisting essentially of α-amino-ε-caprolactam which has been first dissolved in an organic solvent.

7. The method of claim 1 wherein the neutralization agent is L-α-amino-ε-caprolactam and further comprising the steps of:
  a. fractionating the solution remaining after removal of the precipitated lysine monohydrochloride to separate the organic solvent from a solution containing L-α-amino-ε-caprolactam hydrochloride;
  b. recycling the organic solvent to the neutralization operation; and
  c. recycling the fractionation residue containing primarily L-α-amino-ε-caprolactam hydrochloride to the hydrolysis step.

8. The method of claim 1 wherein the neutralization agent is D,L-α-amino-ε-caprolactam or D-α-amino-ε-caprolactam and further comprising the steps of:
  a. fractionating the solution remaining after removal of the precipitated lysine monohydrochloride to separate the organic solvent and a portion of the water from the remaining solution;
  b. recycling the organic solvent to the neutralization operation;
  c. filtering to remove the precipitated crystalline D,L-α-amino-ε-caprolactam hydrochloride or D-α-amino-ε-caprolactam hydrochloride for recycle to a resolution operation; and
  d. recycling the filtrate to the neutralization step.

9. The method of claim 1 wherein the neutralization agent is an L-α-amino-ε-caprolactam - transition metal complex chloride salt and further comprising the steps of:
  a. drying the solution remaining after removal of the precipitated lysine monohydrochloride to separate the organic solvent and to remove the water from the crystalline residue;
  b. recycling the organic solvent;
  c. extracting the crystalline residue with an alcohol to separate the crystalline L-α-amino-ε-caprolactam hydrochloride from the alcohol solution containing the transition metal salt;
  d. recycling the extraction residue containing primarily crystalline L-α-amino-ε-caprolactam hydrochloride to the hydrolysis step; and
  e. recycling the alcohol extract containing primarily transition metal salt in the alcohol solution to resolution.

10. The method of claim 9 wherein the L-α-amino-ε-caprolactam transition metal salt is optically impure and wherein D,L-α-amino-ε-caprolactam hydrochloride produced as a byproduct remains dissolved in the alcoholic solution.

11. The method of claim 1 wherein step (a) comprises neutralizing said solution with the nickel chloride complex of α-amino-ε-caprolactam.

12. The method of claim 1 wherein said transition metal complex chloride salt is employed as a neutralization agent.

* * * * *